United States Patent
Rivet, II et al.

(10) Patent No.: US 11,986,361 B2
(45) Date of Patent: May 21, 2024

(54) STENT RETRIEVER CLEANING DEVICES AND METHODS

(71) Applicant: Virginia Commonwealth University, Richmond, VA (US)

(72) Inventors: Dennis J. Rivet, II, Richmond, VA (US); Shane Diller, Richmond, VA (US); John F. Reavey-Cantwell, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 17/455,316

(22) Filed: Nov. 17, 2021

(65) Prior Publication Data

US 2022/0151730 A1 May 19, 2022

Related U.S. Application Data

(60) Provisional application No. 63/114,703, filed on Nov. 17, 2020.

(51) Int. Cl.
| *A61B 90/70* | (2016.01) |
| *B08B 9/023* | (2006.01) |
| *B08B 9/032* | (2006.01) |
| *B08B 11/02* | (2006.01) |
| *A61B 17/221* | (2006.01) |

(52) U.S. Cl.
CPC .............. *A61B 90/70* (2016.02); *B08B 9/023* (2013.01); *B08B 9/0321* (2013.01); *B08B 11/02* (2013.01); *A61B 17/221* (2013.01); *B08B 2209/032* (2013.01)

(58) Field of Classification Search
CPC ..... A61B 90/70; A61B 17/221; A61B 90/701; B08B 9/023; B08B 2209/032; B08B 11/02
See application file for complete search history.

(56) References Cited

U.S. PATENT DOCUMENTS 4,288,882 A * 9/1981 Takeuchi ............... A61B 1/122
15/97.1
5,090,433 A * 2/1992 Kamaga ................. A61B 1/122
134/182

(Continued)

FOREIGN PATENT DOCUMENTS

DE 20107405 U1 * 8/2001 ............. A61B 50/20
DE 202005015801 U1 * 1/2006 ............. A61B 50/20

(Continued)

*Primary Examiner* — Joseph L. Perrin
*Assistant Examiner* — Irina Graf
(74) *Attorney, Agent, or Firm* — WC&F IP (57) ABSTRACT

An exemplary device is indicated for use in physically debriding thrombus fragments from a stent retriever, using hospital-grade saline, or heparinized saline, for example. This device may be used in the sterile field, during a mechanical thrombectomy procedure. An exemplary cleaning device for cleaning a stent retriever within a sterile surgical field may include a chamber configured to receive and enclose a stent retriever to be cleaned, at least one port configured for connection with a fluid source to enable inflow and/or outflow of a fluid to or from the chamber, and one or more support structures configured to support the stent retriever in a fixed position inside the chamber.

19 Claims, 10 Drawing Sheets

(56) References Cited

U.S. PATENT DOCUMENTS

| | | | | |
|---|---|---|---|---|
| 5,333,606 A * | 8/1994 | Schneider | ............. | F16K 5/0207 285/332.1 |
| 5,354,267 A * | 10/1994 | Niermann | ......... | A61M 16/0463 128/207.14 |
| 5,492,671 A * | 2/1996 | Krafft | ....................... | A61L 2/26 422/26 |
| 6,217,564 B1 * | 4/2001 | Peters | ................ | A61M 39/165 604/905 |
| 6,325,080 B1 * | 12/2001 | Held | ....................... | A61B 1/123 134/169 R |
| 6,554,808 B1 * | 4/2003 | Cook | .............. | A61M 25/09041 604/265 |
| 8,623,149 B2 * | 1/2014 | Bettencourt | ............ | B08B 5/026 134/122 R |
| 9,993,145 B2 * | 6/2018 | Yamaya | ............. | A61B 1/00098 |
| 2002/0138126 A1 * | 9/2002 | Camrud | ................ | A61B 90/70 623/1.11 |
| 2004/0118440 A1 * | 6/2004 | Sasaki | .................... | A61B 90/70 134/169 C |
| 2011/0005556 A1 * | 1/2011 | Kawase | ................ | A61B 1/125 134/166 R |
| 2011/0132404 A1 * | 6/2011 | Lutz | ........................ | A61L 2/18 134/34 |
| 2013/0319888 A1 * | 12/2013 | Birkbeck | ................ | A61B 50/30 206/370 |
| 2014/0166054 A1 * | 6/2014 | Moberg | ................ | B08B 9/0328 134/22.12 |
| 2014/0209121 A1 * | 7/2014 | Kamen | ................ | B08B 3/047 206/6.1 |
| 2014/0316380 A1 * | 10/2014 | Davis | .................... | A61M 25/00 604/523 |
| 2015/0069728 A1 * | 3/2015 | Seitz, III | ............... | A61M 25/00 206/305 |
| 2015/0250550 A1 * | 9/2015 | Dawson | ................. | A61B 50/39 134/42 |
| 2015/0305819 A1 * | 10/2015 | Krause | ................... | A61B 90/70 134/8 |
| 2015/0342694 A1 * | 12/2015 | Morejon | ................ | A61B 90/70 134/166 C |
| 2015/0352325 A1 * | 12/2015 | Quick | ................ | A61B 17/221 606/127 |
| 2015/0359599 A1 * | 12/2015 | Fagan | ....................... | B08B 3/04 134/116 |
| 2015/0374401 A1 * | 12/2015 | Guggenheimer | ..... | A61M 25/00 606/114 |
| 2016/0067004 A1 * | 3/2016 | Geddis | ................... | A61B 90/70 134/169 C |
| 2016/0193012 A1 * | 7/2016 | Anderson | ............. | A61B 34/30 606/130 |
| 2016/0278876 A1 * | 9/2016 | Garvey | ................... | A61B 90/70 |
| 2017/0065368 A1 * | 3/2017 | Garvey | ................. | A61B 90/70 |
| 2018/0147022 A1 * | 5/2018 | Gupta | .................... | A61B 90/70 |
| 2019/0150722 A1 * | 5/2019 | Yamaya | ............. | G02B 23/2476 |

FOREIGN PATENT DOCUMENTS

| | | | | |
|---|---|---|---|---|
| DE | 102004053355 A1 * | 5/2006 | ............. | A61B 50/20 |
| DE | 202006019668 U1 * | 4/2007 | ............. | A61B 50/20 |
| EP | 1839683 A1 * | 10/2007 | ............. | A61B 50/22 |

* cited by examiner

DETAIL H

SECTION J-J

Figure 10

SECTION C-C

*Figure 17*

DETAIL D

*Figure 18*

DETAIL E

SECTION K-K

Figure 21

DETAIL L

STENT RETRIEVER CLEANING DEVICES AND METHODS

CROSS-REFERENCE TO RELATED APPLICATIONS

This application claims the benefit of U.S. Provisional Application No. 63/114,703, filed Nov. 17, 2020.

FIELD OF THE INVENTION

Embodiments of the invention generally relate to operating room equipment and, in particular, devices and methods for cleaning stent retrievers.

BACKGROUND

Every year there are more than 795,000 people who have a stroke, and over 87%, approximately 691,000 of these are ischemic strokes. Ischemic stroke is a condition that results from decreased blood flow to the brain, and while this can result from low blood pressure (hypotension), this is more traditionally due to a blood clot becoming lodged in the blood vessels of the brain, and blocking blood flow. This requires emergency surgical intervention by an endovascular surgeon to remove the blockage as decreased blood flow to the brain can cause permanent neural damage in as little as 3 hours, but most patients do not arrive at the hospital until at least 8 hours have passed. Over 70% of the stroke cases are due to blockage of the anterior circulation, and of these, blockage of the middle cerebral artery is the most common.

There are various methods to clear the clot, one being mechanical thrombectomy. One thrombectomy method requires first using a guidewire to pierce the blood clot, and passing a catheter over this wire, then removing the wire, and inserting the stent retriever. This stent retriever will deploy distally to the insertion point and then when dragged backwards, will capture the blood clot in the mesh of the stent retriever, and pull it backwards through the catheter and out of the body via the incision site. Another thrombectomy technique utilizes direct aspiration of the thrombus through and via a catheter that is advanced up to the proximal interface of the thrombus. The aspiration is typically performed by one of the commercially available pumps made for this application. The two techniques are often performed in a combined manner whereby a stent retriever is deployed across the thrombus and an aspiration catheter that is co-axial to the stent retriever wire is advanced to the proximal face of the thrombus. They are then removed together, in tandem.

The number of mechanical thrombectomies has been increasing since 2015. Approximately 2% to 3% of thrombectomies were mechanical in 2016. An estimated 10% of patients presenting with ischemic stroke are eligible for this treatment. Of the 691,000 ischemic stroke cases per year, that means 20,000 cases are being treated with mechanical thrombectomy but up to 69,000 could be performed each year.

Currently, there are three FDA approved stent retrievers in use in the United States, respectively manufactured by Medtronic, Cerenovus, and Stryker. Existing products have different morphologies, ranging from spiral stents, to double lumen stents, to hexagonal mesh, to self deploying stents. Due to the small diameter blood vessels in the brain, these stents are often only 4-5 mm in diameter, and range from 24-40 mm in length, and are often composed of a Nitinol or Stainless Steel mesh. They range in price from $7,000 to $10,000. Each stent comes in a sterile package and is approved for up to 3 passes, which means the stent can be removed, cleaned, and then reinserted up to 2 times. In many surgeries, the retrieval of the blood clot is not immediately successful, known as first pass success.

There are many reasons that there is a low first pass success rate of only 25% and many problems that can arise when performing this procedure. For instance, the diameter of the blood vessel changes significantly along this 40 mm path, from 2.2 mm in diameter to around 1.2 mm in diameter and the stent expands to accommodate this change. As the stent is retrieved, it expands, and the blood clot may loosen and be lost. In addition, there is no tactile or mechanical feedback for the surgeon to know that the clot has been captured or lost by the stent. The blood clot itself is composed of fibrinogen and coagulated blood, which may tear or fragment while being retrieved. Since the surgeon has no method of knowing if the clot is tearing or has torn, the only indication is visual once the stent has been removed from the catheter. The surgeon then has to decide whether to clean the stent off and perform another pass, or open a new stent package.

The current method for cleaning a stent off is by using a syringe to squirt sterile saline in the open, agitate the device while submerged in saline in a bowl or tray, or some combination of these. These techniques are time consuming, sometimes ineffective, and may even incompletely remove some thrombus debris. Alternatively, the surgeon or other member of the procedural team may have to try to physically remove the blood clot manually or with an instrument, but due to the small size and mesh structure, stents can be damaged and will not redeploy correctly. It may also cause unrecognized damage to the device which goes unrecognized, leading to either less efficacious function and/or iatrogenic injury to the vessel with the device. Stents of stent clot retrievers are often only 3-6 mm in diameter and 40-60 mm long, and so they are incredibly fragile. These stents are attached to a tail wire that is typically 100 cm long. If the stent is damaged, a new stent must be opened. Though there are multiple manufacturers of stents in the United States, there is no commercial device to clean the stent for reuse during surgery.

SUMMARY

Embodiments of the disclosure provide a device to rapidly and efficiently remove thrombus and blood products from stents during a mechanical thrombectomy or similar procedure. The generally handheld device includes a small (e.g., approximately 5 to 10 cm) chamber in which a stent retriever may be placed for cleaning and subsequent reuse. The device is compatible for use with sterile syringes and saline or other liquid commonly found on the surgical field during an endovascular procedure. Specifically, the device may include one or more syringe connections to assist in the cleaning of the stent retriever. The syringes attach to the chamber via a luer lock fitting for a secure connection. The syringes are used to injected fluid into the chamber and remove fluid from the chamber cyclically. The design of the inflow and interior portion of the chamber is such that the fluid agitation and propellant force are maximized to clean the debris from the stent tines.

The stent retriever is held within the chamber with the delivery wire extending out of the chamber on the surgical field. The device preferably has a viewing area, such as a transparent wall, that allows the operator to immediately visualize the status of the cleaning process without opening the cleaning chamber. The device has least two ports to allow inflow and outflow to/from the chamber at the same time. The two ports allow for operation with one or two syringes to provide the flushing flow of the cleaning solution in and out of the chamber simultaneously.

The inflow rate and directionality of the wash fluid is partly influenced by the port placement about the chamber, which may vary among embodiments, but which in all cases is configured to maximize the rate and degree of success in cleaning debris from the stent retriever. Currently, there is no technology or specific devices to clean stents that are designed to improve efficiency and safety in this procedure compared with direct cleaning by hand in a bowl or tray of water. Besides offering rapid cleaning and preparation of a stent retriever for additional uses or "passes" during a single mechanical thrombectomy or similar procedure, exemplary devices allow for collection of thrombus specimen for pathological examination, research purposes, or other use. The device may be used during all mechanical thrombectomies or embolectomies which are performed with a stent retriever.

Advantages of present embodiments include but are not limited to reduced operating room (OR) time spent cleaning a stent retriever, cleaner stent retrievers, and reduced risk of damage to stent retrievers during cleaning. Significantly, the device can remove the thrombus from the stent without requiring mechanical manipulation by the surgeon. Further, this device should aid in the rinsing syringe being able to collect the removed blood clot debris, as these samples are often sent off to a testing facility for composition testing.

The device is operable with only a manual wash cycle. Sufficient turbulence is created inside a small chamber via hand operated syringes. By limiting the internal volume of the chamber, a standard e.g. 20 ml syringe may be used. An agitated fluid can be created by rapidly cycling the plunger of the syringe in and out, which results in a pressure differential and moves the fluid over the stent retriever very rapidly.

Exemplary embodiments include a cleaning device alone. Exemplary embodiments further include a kit for a mechanical thrombectomy procedure, comprising a stent retriever and a cleaning device together, where the cleaning device is configured (e.g., in size and shape) for compatibility with the stent retriever. An exemplary cleaning device for cleaning a stent retriever within a sterile surgical field may include a chamber configured to receive and enclose a stent retriever to be cleaned, at least one port configured for connection with a fluid source to enable inflow and/or outflow of a fluid to or from the chamber, and one or more support structures configured to support the stent retriever in a fixed position inside the chamber. The chamber is configured to be used to sufficiently remove debris from the stent retriever to permit reuse of the stent retriever during a single thrombectomy procedure.

DETAILED DESCRIPTION

Figure 1A:
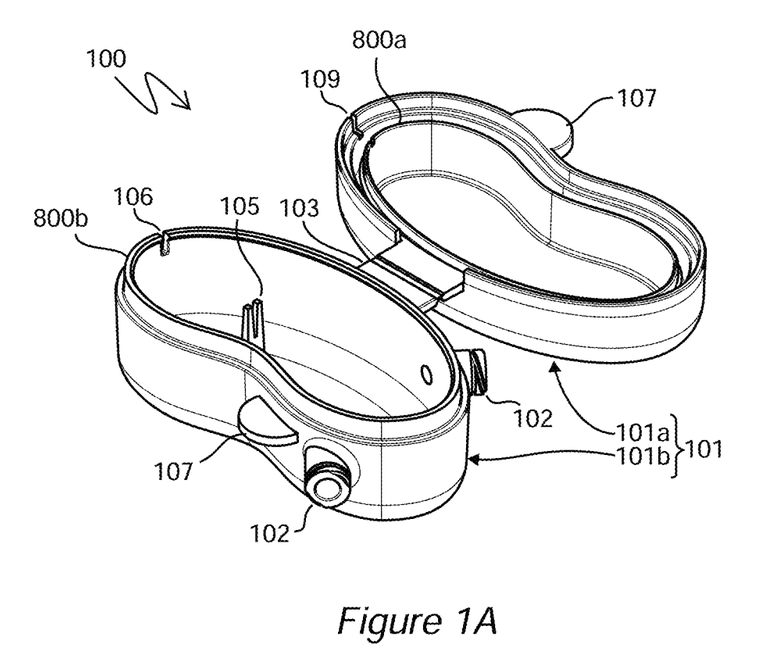
FIG. 1A is a perspective view of an exemplary device in an open state.
Figure 1B:
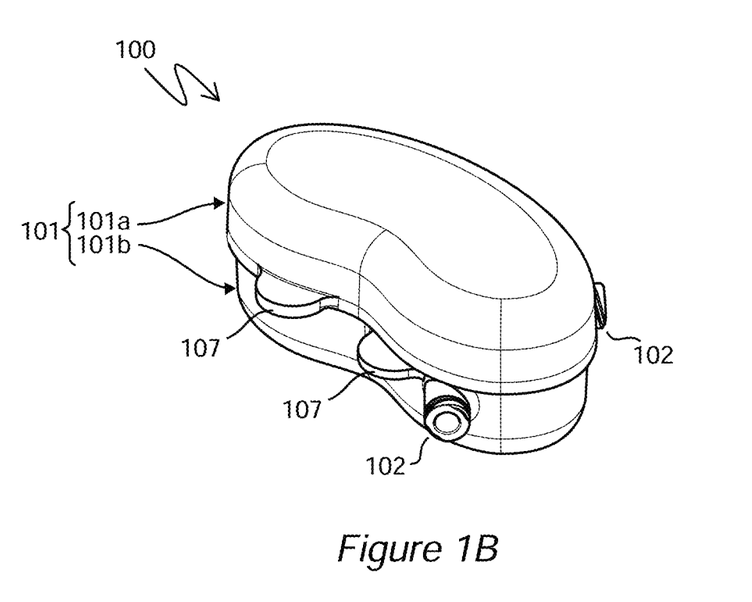
FIG. 1B is a perspective view of the exemplary device in a closed state.
Figure 2:
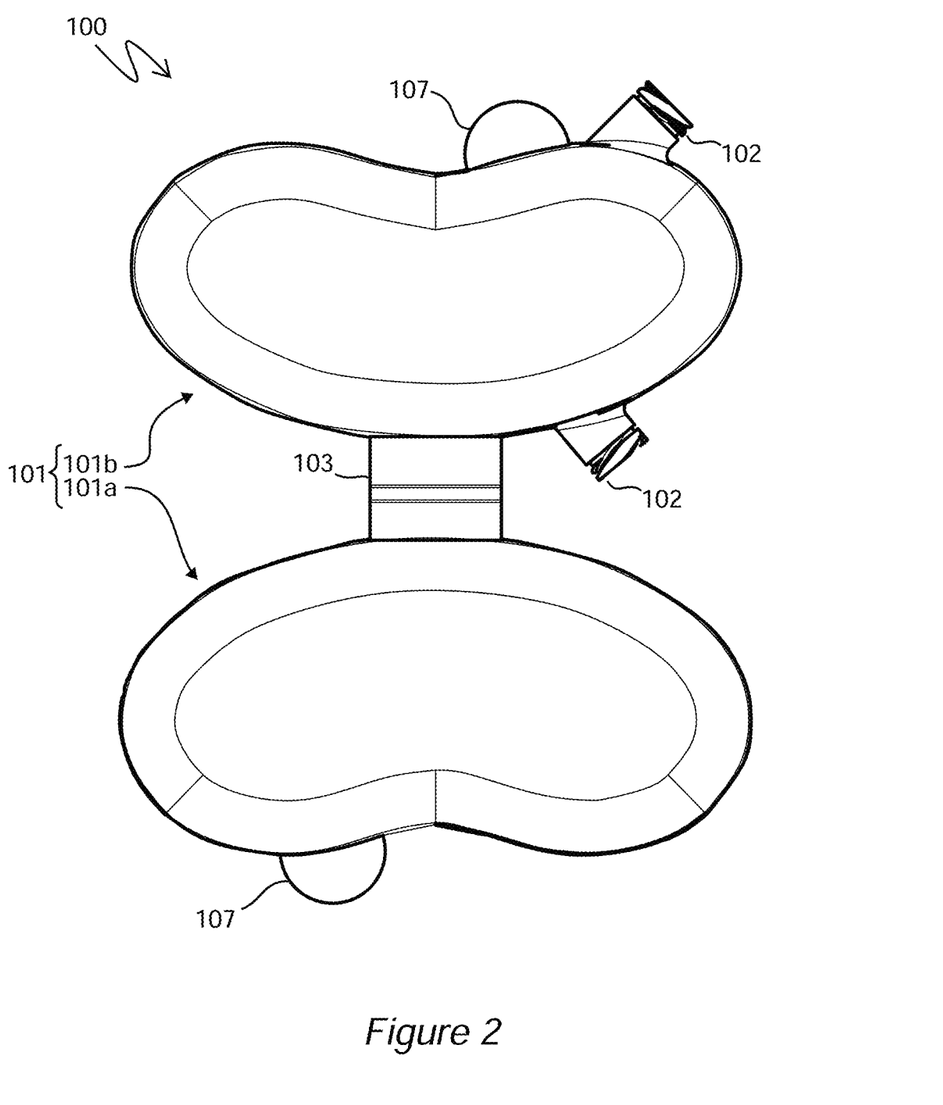
FIG. 2 is a plan view of the exterior surfaces of the exemplary device in the open state.
Figure 3:
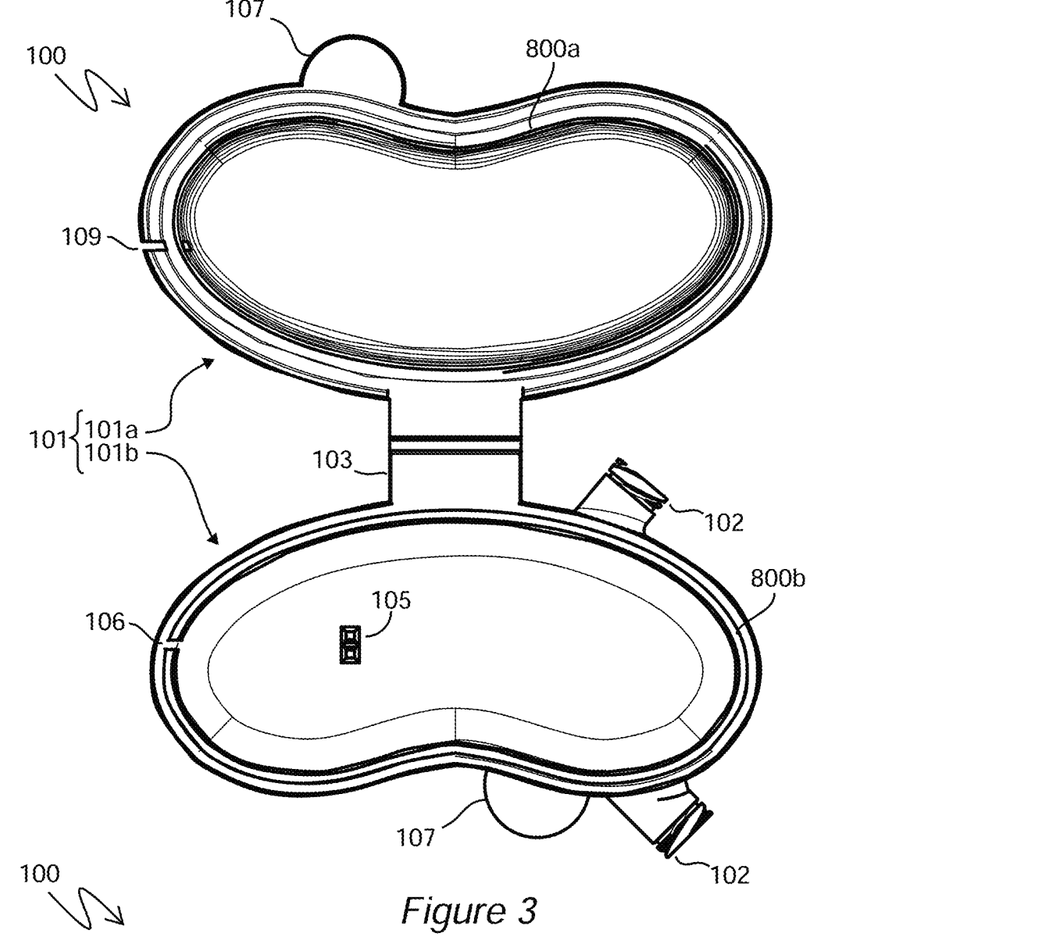
FIG. 3 is a plan view of the interior surfaces of the exemplary device in the open state.
Figure 4:
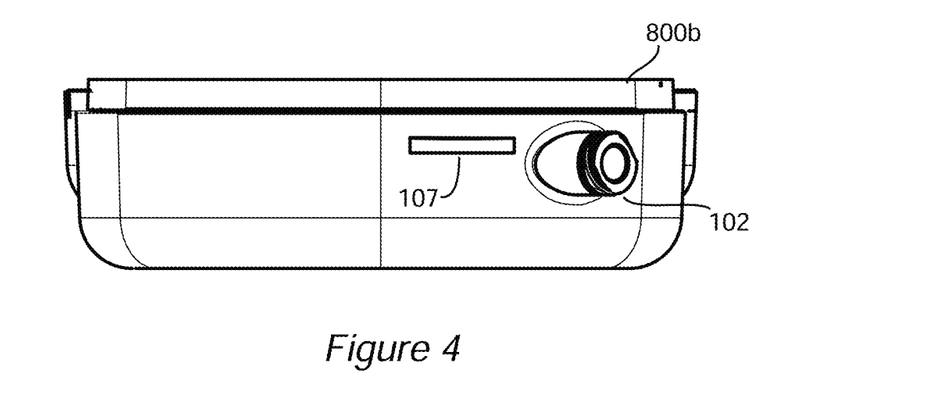
FIG. 4 is a first side view of the exemplary device in the open state.
Figure 5:
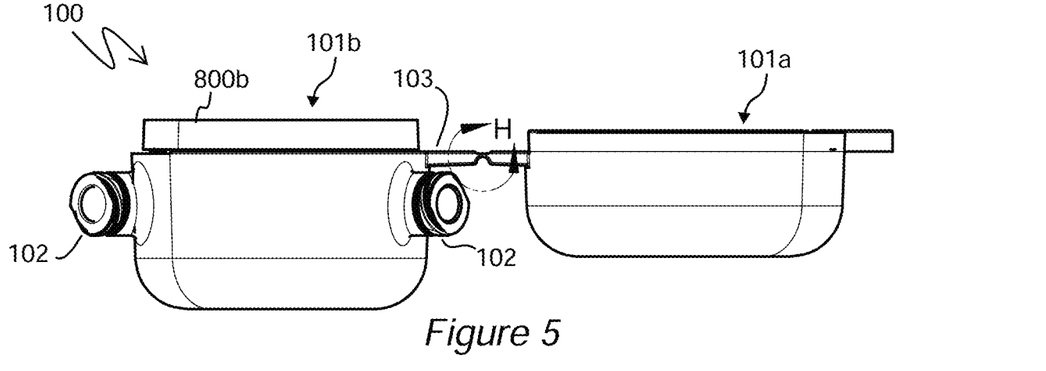
FIG. 5 is a first end view of the exemplary device in the open state.
Figure 6:
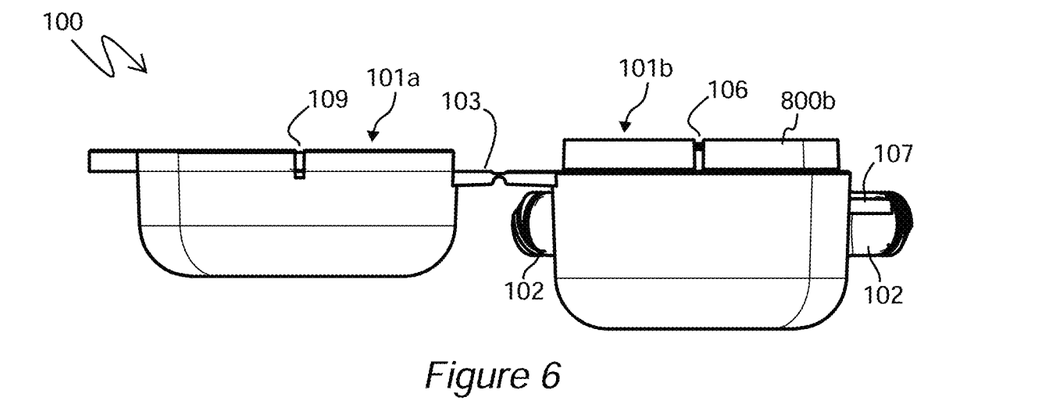
FIG. 6 is a second end view of the exemplary device in the open state.
Figure 7:
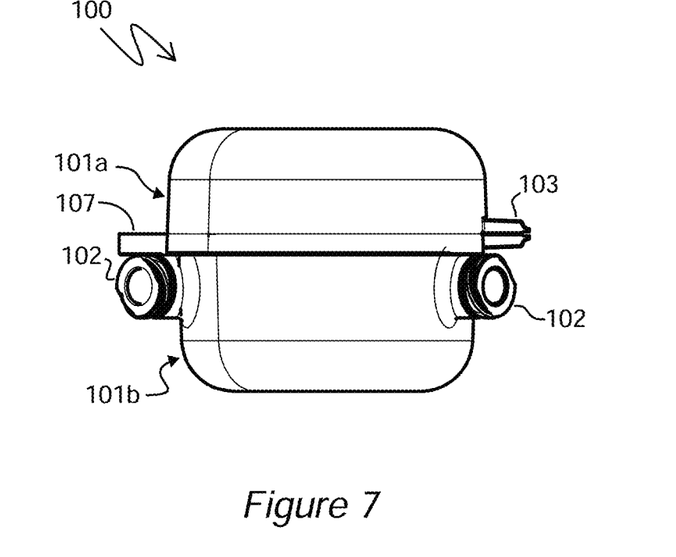
FIG. 7 is the first end view of the exemplary device in a closed state.
Figure 8:
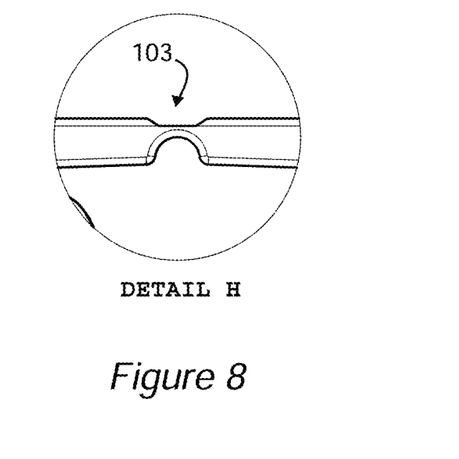
FIG. 8 is an enlarged view taken from FIG. 4 showing a living hinge.
Figure 9:
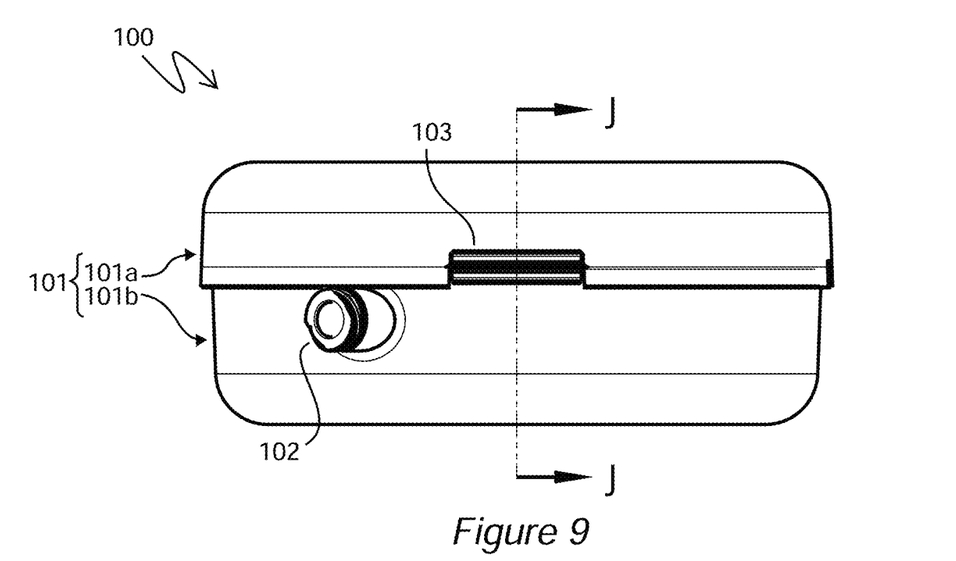
FIG. 9 is a second side view of the exemplary device in the closed state.

FIGS. 1A and 1B depict an exemplary medical device 100 to remove blood clot debris from a stent retriever during a mechanical thrombectomy procedure. FIGS. 2-19 present alternative views of the same device 100. The cleaning performable with the device 100 allows the stent retriever to be reinserted into an artery or vein multiple times, saving the expense of multiple stent retrievers which can easily cost $7,000 to $10,000 per stent package. For purposes of this disclosure, the terms "stent", "stent retriever", and "stent clot retriever" may be used interchangeably.

The exemplary device 100 comprises a hinged chamber 101 that has two ports 102 with attachments for connecting the chamber interior to fluid sources such as syringes. The attachments may be, for example, luer tapers (e.g., locking or slipping type luer tapers, e.g., luer locks). The luer tapers may be molded into the chamber wall such that the bottom 101*b* (or lid as the case may be depending on the port's location) and the luer port are a single item of continuous material. The chamber 101 is created by the combination of a lid 101*a* and bottom 101*b*. One or else both the lid 101*a* and bottom 101*b* are shaped as a cup or basin, that is to say a structure having walls positioned to hold and retain matter, in particular a liquid. The device 100 may be a single plastic injection molded part with a living hinge 103 and an annular snap fit ring 800 (see the cross-sectional view of FIG. 10 for a clearer depiction of the snap fit ring). Note that as used in this disclosure, both "annular" and "ring" refer to a loop, generally a closed loop, and may but not necessarily mean a symmetrical loop, e.g., a circular ring or the like.

The two ports 102 may be configured as female luer ports that attach to any standard male syringe part. One or more male luer caps may be used with the device 100 for any user who wishes to block one of the ports and use the device with a fewer number of syringes than there are ports, e.g., a single syringe for a two port device 100. Exemplary washing, discussed below, may be achieved with either one or multiple (e.g., two) syringes attached. The device 100 is recommended to be used with e.g. 15 ml to 20 ml of sterile saline (or more) to remove a thrombus and/or any other debris from a stent retriever enclosed by the chamber 101.

A support arm 105 projects from a wall of the chamber 101 to support an inserted stent retriever at a fixed position away from the walls of the chamber 101. The support arm 105 may project from either, or both, the lid 101a or bottom 101b. The support arm may be configured to require the stent retriever to clip in, e.g., by way of a cut-out in the arm that is slightly smaller than the size of a stent retriever tail wire. A window, slot, or hole 106 serves as a second support structure of support for the stent retriever as well as a means for a tail wire, which may be 100 cm or more in length, to project out from the interior of the chamber 101. The lid 101a has a window, slot, or hole 109 corresponding in circumferential position with hole 106 of bottom 101b. The lid 101a and bottom 101b have overlapping circumferential lips when the chamber 101 is closed, and in such closed state the holes 106 and 109 also overlap so that a through-hole from the interior of the chamber 101 to the exterior environment remains. The tail wire for which the holes 106/109 are provided is so long due to the incision site for the surgery often being in the wrist or abdomen. The optimal orientation of the tail wire during cleaning is lateral from the operator as this can be laid in the sterile field or held by an assistant. This would decrease the chance of the tail wire being stepped on or falling out of the sterile field.

In some embodiments, an o-ring or a deformable seal may be provided at or instead of holes 106/109. The deformable seal, e.g. a rubber gasket or the like, may seal the edge of the chamber when no tail wire is present but deform to permit the through passage of the tail wire when the wire is present. According to the exemplary embodiment of device 100, an inserted stent retriever makes contact with the device 100 at only two places, namely the support arm 105 and the hole 106/109. The minimal points of physical contact of an inserted stent retriever with the device 100 reduces the risk of physical damage to the stent retriever, a significant advantage given the typical fragility of stent retrievers.

The device 100 is intended for ease of use by any physician or medical staff trained to perform or assist with the treatment of ischemic stroke or interventional neuroradiology, or any other procedure requiring removal of blood clots. The device 100 is ergonomic and usable without any supplemental tools besides one or two syringes attachable to the ports 102.

Figure 17:
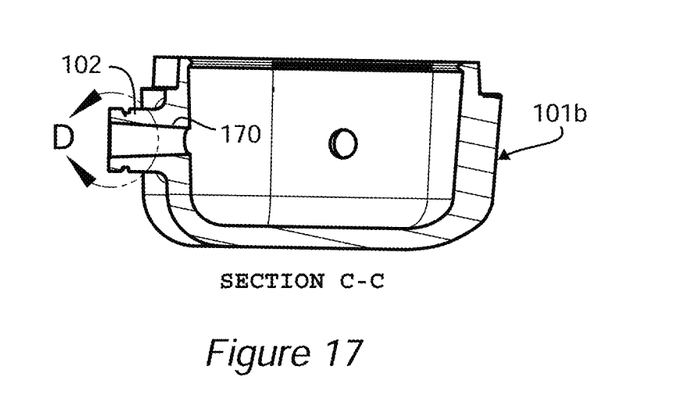
FIG. 17 is a sectional view of the exemplary device taken along line C-C in FIG. 14.
Figure 18:
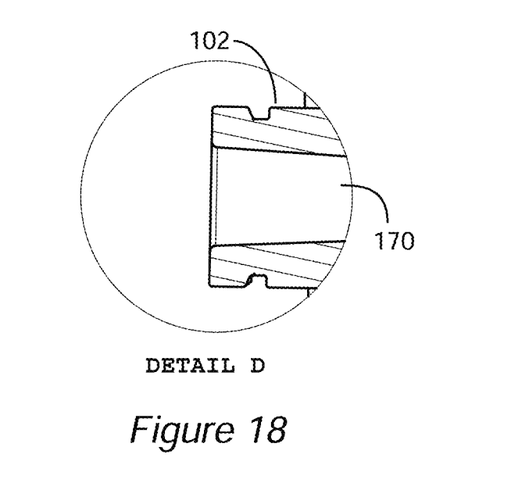
FIG. 18 is an enlarged view taken from FIG. 17 showing a luer lock cross section.
Figure 19:
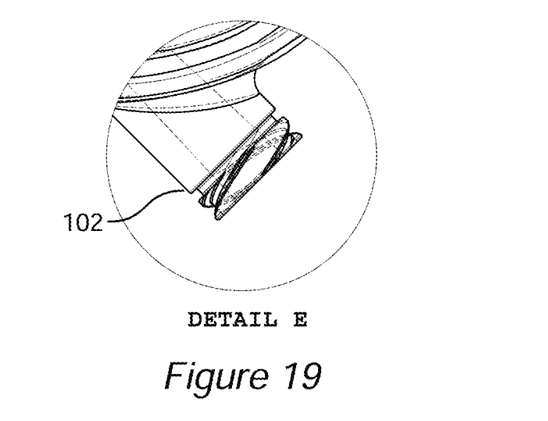
FIG. 19 is an enlarged view taken from FIG. 14 showing the luer lock.

FIGS. 17, 18, and 19 illustrate ports 102 in more detail. The ports may be configured for attachment to syringes, or else the ports may be configured for attachment to other fluid sources. External fluid sources may be attached with a twist-on, clip-on, snap-on, friction fit, or other type of connection that permits a secure attachment for the duration of use of the wash chamber while permitting fluid to easily pass through the channel 170 of each respective port 102.

The shape/profile of the exemplary device 100 is curved. For the illustrative embodiment in the figures, the curvature is specifically a bean shape (e.g., kidney-bean shape). The device 100 is preferably configured to be handheld, according to its size, weight, and shape. A curved shape is advantageously more comfortable and secure to hold. At least the largest face of bottom 101b is flat to provide a reliable contact surface with a table or medical tray, and the largest face of lid 101a may also be flat or relatively so to allow a user to set the device down on either of the opposing sides without a risk of the device rolling or moving by accident. The flat side, or sides, prevent the device 100 from rolling off a table and out of the sterile field.

The bean-shape is exemplary because it accounts for the nature of handheld use and ergonomics. The shape is configured for easy gripping and handling by a single operator. The user's hands will generally be covered by surgical gloves, often wet. Accordingly, the total size of the device is configured to minimize the risk of slippage when being held and handled. An exemplary size range is 3 to 5 inches in length, or 3.5 to 4 inches in length, based on the size of FDA approved stent retrievers and e.g. the grip of the average human adult. An exemplary non-limiting maximum width is 1 to 1.5 inches, in consideration of 6 mm being the widest stent retriever on the market. When closed, the device may be 1-2 inches, e.g. 1.25 in, tall. As further non-limiting but exemplary dimensions, the device 100 may be sized and configured to accommodate stent retrievers from 3-6 mm in diameter, and 24-45 mm in length. The general cavity size within the chamber 101 is such that the device 100 is compatible for use with most if not all stent retriever morphologies commercially available at the time this disclosure was written. Generally a single device 100 will be sized and configured to fit a hold a single stent retriever at a time. The internal volume of the chamber 101 may be e.g. 300 ml or less, or 250 ml or less, 200 ml or less, 190 ml or less, 180 ml or less, 170 ml or less, 160 ml or less, or 150 ml or less.

The lid 101a and bottom 101b of chamber 101 are connected to one another, preferably permanently in some embodiments. The connection may be made at the time of manufacture, or else the device may be produced as two pieces that are assembled (e.g., snapped together) for use. A tether is one option for a connection. An exemplary option is a hinge, e.g. a living hinge 103. A living hinge reduces assembly time in the Operating Room and enhances human factors in handling of the device with one hand. Exemplary embodiment can be closed with just one hand. The living hinge results in the lid staying attached to the bottom at all times. The hinge 103 is configured for repeated flexure. An exemplary material is polypropylene, which is both capable of repeated flexure and is not prone to warping when producing by a plastic injection molding process.

Exemplary wash chambers are able to accommodate one or more of the commercially available stent retrievers, presently made by Stryker, Cerenovous, Medtronic and Penumbra. All four companies produce different morphologies of stents, yet some exemplary embodiments are shaped and sized in both chamber and support structures to effectively wash all four or more than four different morphologies.

As mentioned above, a substantially watertight seal is desirable when the chamber 101 is closed in exemplary embodiments, at least for most if not the entire rim where the lid 101a and bottom 101b meet, with the possible exception of the hole 106/109 provided for the stent tail wire. The hole 106/109 is nevertheless desirable to avoid deformation of the tail wire. A deformed tail wire can cause problems when redeploying the cleaned stent retriever in the narrow blood vessels.

To create a tight seal that is at least semi-watertight, substantially equal pressure is exerted about all sides of the device 100 when closed. The curved shape/profile of the chamber 101 provides not only an ergonomic benefit, as discussed already, but a better seal than a shape having any square corners. Said differently, some exemplary embodiments preferably have a shape without any corners, especially sharp corners such as ninety degree corners, to provide improved sealing along the edges where the lid 101a and bottom 101b meet. The snap fit ring may be configured to seal an interface between the bottom and the lid of the chamber for at least 95%, or at least 98%, or at least 99%, of the interface. In addition, it is generally desirable that the device comprise one or more fasteners that create a positive holding which holds the bottom and the lid together. Accordingly a positive user applied force is required to separate the top from the bottom after closure to overcome the holding force created by the fastener. The holding force is desirably relatively high, making it difficult to separate the bottom and lid by accident. Physical lips/levers 107 are provided on each of the lid 101a and bottom 101b to provide leverage points for a user to manually overcome the forces holding the chamber 101 shut after closure. The levers 107 create a simple lever that results in the user needing to apply less than the holding force to overcome the holding force. The provision of levers 107 at only specific regions about the chamber 101 and not at any other regions reduces the likelihood of accidental opening of the chamber 101. The levers 107 may be thumbcatches, e.g. physical grooves or tabs, that can be used to create enough force to pull the tooth upward out of the groove.

The holding force required to keep the lid 101a and bottom 101b tight to one another absent user force applied to levers 107 may be provided by one or more of different types of fasteners.

The exemplary embodiment depicted by FIGS. 1A, 1B, and 2-19 comprises a fastener configured as an annular snap fit structure. The snap fit ring 800 includes a first ring 800a and a second ring 800b. The rings 800a and 800b together form an interlocking arrangement when the chamber 101 is closed. The snap fit ring 800 appears in several figures, but its functional features are perhaps most easily viewed in FIGS. 10, 12, 13, 15, and 16. The bottom 101b comprises a first projection 801 of ring 800b. The lid 101a comprises a second projection 802 of ring 800a. The projections 801 and 802 engage one another when the chamber 101 is closed. The snap fit projection 802 is put under stress, substantially perpendicular to the long axis of surface 804, and deforms as the two halves 101a and 101b of the chamber 101 are brought together. The lid 101a comprises a channel or groove 803 with an inner wall 804 and outer wall 805. The projection 802 projects from the wall 804 toward the wall 805. The distance between the wall 804 and wall 805 is generally greater than the distance between the tip of projection 802 and wall 805. This gap is sized to be smaller than projection 801. Closing of chamber 101 therefore requires a positive applied force to force projection 801 past the gap between projection 802 and wall 805. The force causes a temporary deflection of projection 802 away from wall 805. To reduce the stress in the snap-fit projections, and prevent failure, small fillets may be included at the points at which the snap-fit projections meet the walls from which they protrude.

Figure 10:
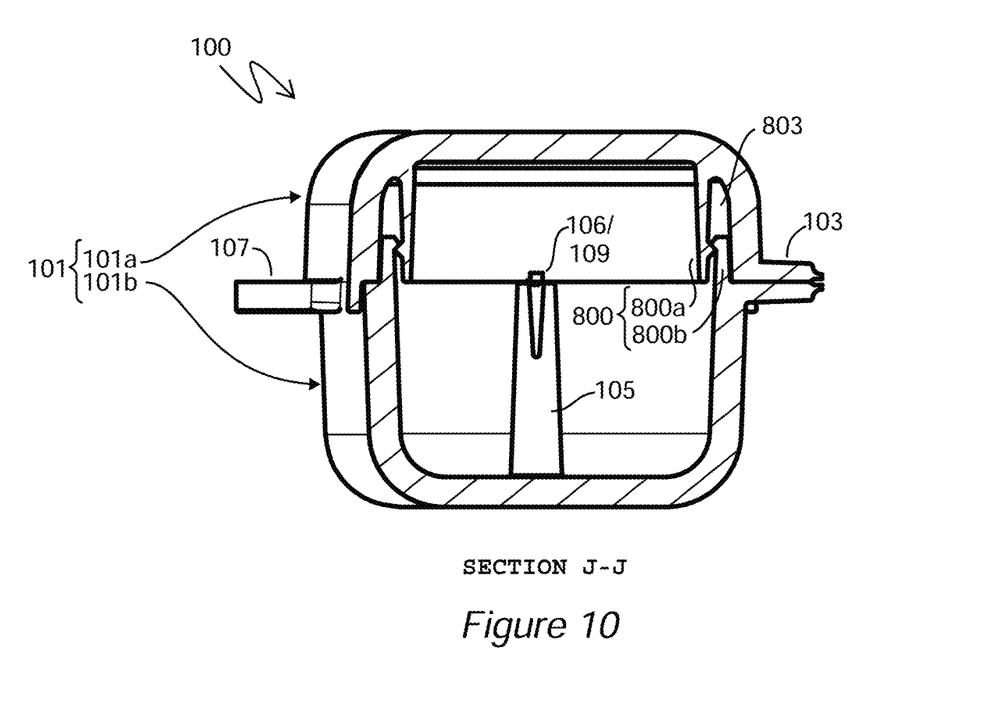
FIG. 10 is a sectional view of the exemplary device taken along line J-J in FIG. 9.
Figure 11:
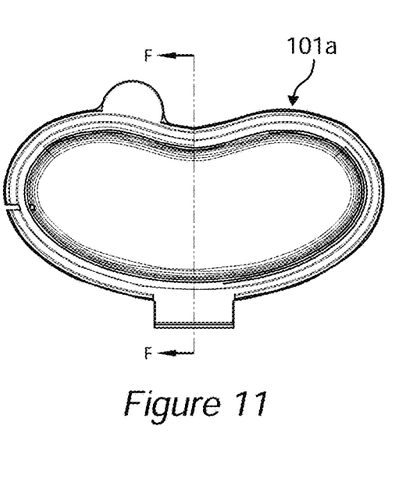
FIG. 11 is a plan view of the lid part of the exemplary device.
Figure 12:
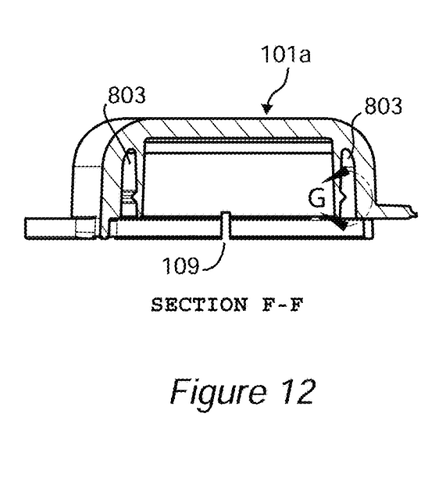
FIG. 12 is a sectional view of the exemplary device taken along line F-F in FIG. 11.
Figure 13:
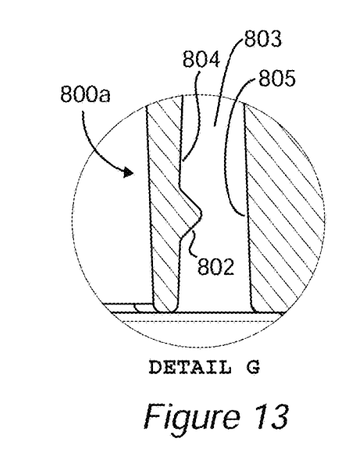
FIG. 13 is an enlarged view taken from FIG. 12 showing a first part of a fastener.
Figure 14:
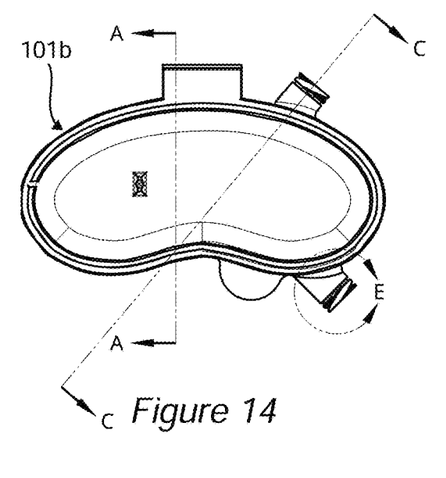
FIG. 14 is a plan view of the bottom part of the exemplary device.
Figure 15:
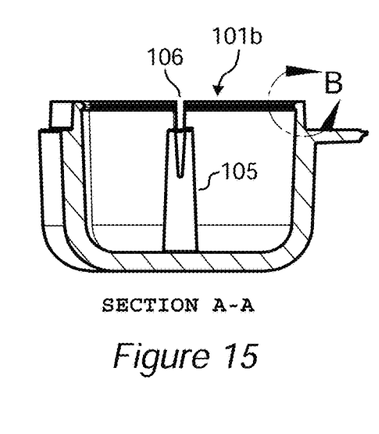
FIG. 15 is a sectional view of the exemplary device taken along line A-A in FIG. 14.
Figure 16:
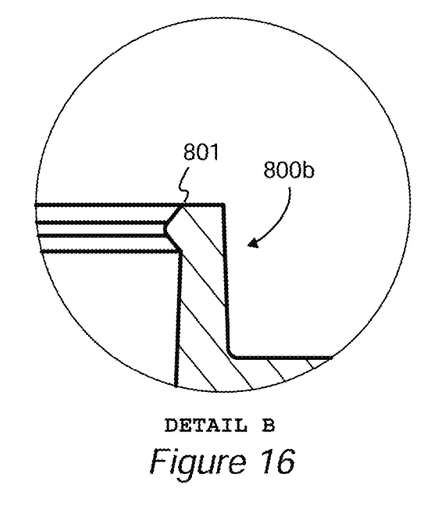
FIG. 16 is an enlarged view taken from FIG. 15 showing a second part of the fastener.

Once the projection 801 is past the gap between projection 802 and wall 805, the projection 802 elastically returns to its original position, effectively trapping the projection 801 in the groove 803 in the absence of external forces providing for another deflection of projection 802 away from wall 805. In sum, the arrangement of projections 801 and 802 creates a "snap" fit of the rings 800a and 800b. The arrangement depicted by FIG. 10 is a mated configuration, during which state the projections may be in nearly or entirely unstressed states (from lack of deflection) while keeping the lid 101a and bottom 101b together as they are manipulated by a user. A small amount of maintained deflection and material stress in the closed state may be desirable to keep the rings 800a and 800b in snug contact with one another. In the exemplary embodiment illustrated, the projections 801 and 802 are both annular. Both projections form a closed loop about an entire perimeter of the bottom 101b or lid 101a respectively. In alternative embodiments, the projection 801 and/or the projection 802 may be a tooth, repeated at intervals about the perimeter but not continuous about the entire perimeter.

In addition to providing a holding force in the closed state of the chamber, the annular snap fit ring provides a physical barrier to water escaping the chamber without the need for a rubber o-ring or gasket. This advantage both reduces the number of parts and simplifies manufacturability and production costs.

It should be appreciated that the arrangement of the projections 801 and 802 may be inverted in alternative embodiments. As depicted in FIG. 10, the projection on the bottom 101b projects radially inward toward a center of the chamber 101, and the projection on the lid 101a projects radially outward toward an exterior of the device 100 (away from the chamber 101). These positions may be reversed such that the projection on the bottom 101b projects radially outward toward an exterior of the device 100 (away from the chamber 101) and the projection on the lid 101a projects radially inward toward a center of the chamber 101. The groove 803 is not strictly necessary depending on the arrangement of the projections.

The number of snap projections, the depth of each projection, the leading angles, and receding angles all affect the force required to close and open the device and may be configured to meet acceptable and desired force thresholds. Because the snap-fit projections 802 of the lid 101a are meant to interfere and deflect with the projections 801 on the bottom 101b of the device 100, the projections 802 may be made into a cantilevered beam to reduce the likelihood of shearing of the snap-fit projections.

Figure 20:
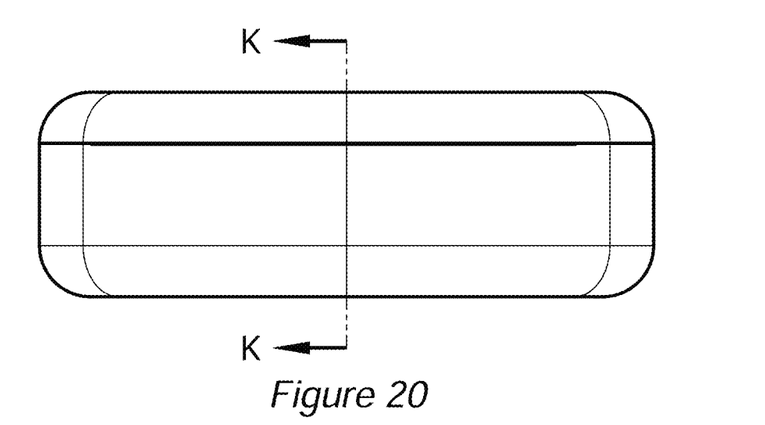
FIG. 20 is a side view of an alternate device embodiment.
Figure 21:
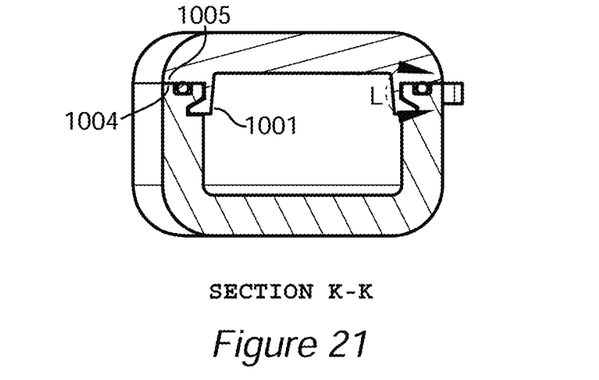
FIG. 21 is a sectional view of the alternate device taken along line K-K and showing a second fastener embodiment.
Figure 22:
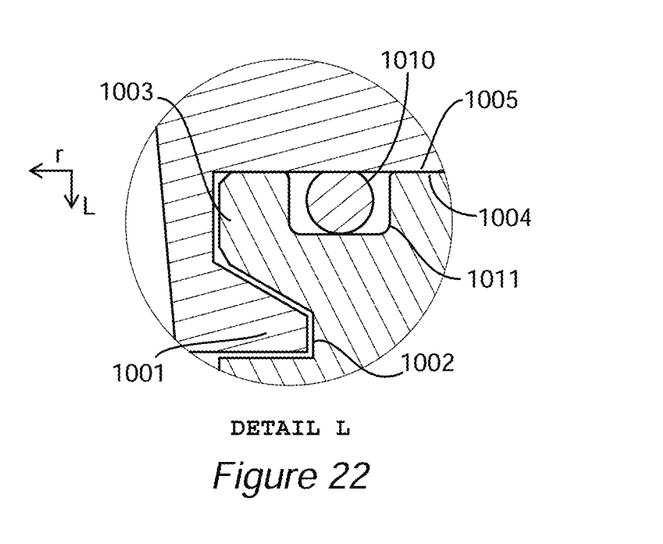
FIG. 22 is an enlarged view taken from FIG. 21 showing the sealing o-ring, seal groove, and snap-fit tooth.

FIGS. 20, 21, and 22 show yet another alternative embodiment for fastening in which a single projection on either the lid or bottom may be paired with a recess on the opposing bottom or lid. FIG. 22 shows a closeup of this type of snap fit configuration. Here, a projection 1001 is configured to deflect in direction r as it passes surface 1003 as projection 1001 is moved in direction L before elastically returning to its original configuration as the projection 1001 slides into recess 1002. It will be appreciated from FIG. 22 that surface 1003 may also be considered a second projection, similar to the snap fit configuration of FIG. 10.

FIG. 22 also shows a rubber ring 1010 that may be positioned at the interface between lid 101a and bottom 101b. An annular recess 1011 may be provided in either the lid or bottom of the chamber into which the rubber ring 1010 may be positioned. Preferably the rubber ring 1010 is sized to deform slightly upon mating of opposing surfaces 1004 and 1005 of the lid and bottom such that the rubber ring 1010 forms a watertight seal. This configuration may be referred to as a flange or face seal o-ring configuration.

Figure 23:
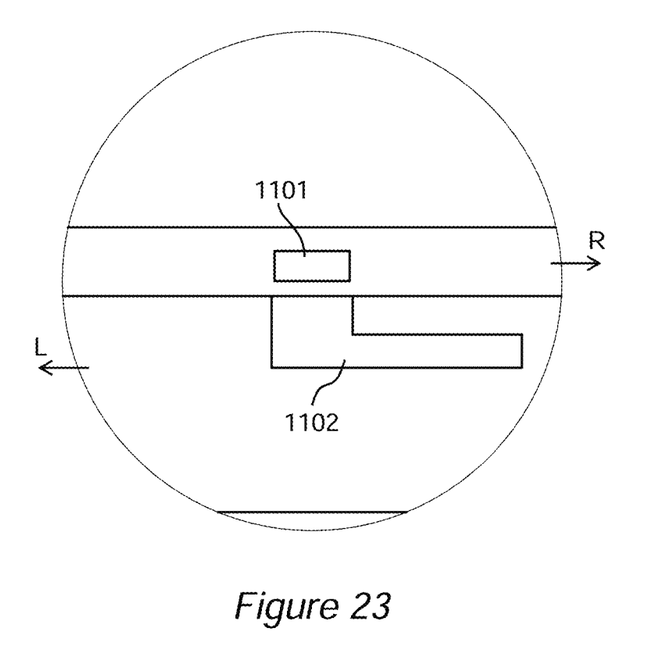
FIG. 23 is an enlarged view of a bayonet fastener.

FIG. 23 shows yet another fastener option for some embodiments. FIG. 23 shows an enlarged view of a bayonet mount to secure two parts together. Named after the method of securing a bayonet to a rifle in close quarters combat, this configuration comprises a pin 1101 and an L shaped slot 1102. The two parts 1101 and 1102 can only come together when the pin and the vertical part of the L slot are aligned, as the presently are in FIG. 23. Then the two elements 1101 and 1102 are twisted (or one is twisted with respect to the other) such that the lid or bottom of the chamber having pin 1101 moves in direction R and/or the bottom or lid of the chamber having slot 1102 moves in direction L. Which part of the chamber—lid or bottom—has the pin which has the slot generally does not matter, meaning either may have the pin and the other have the slot. In any case the pin 1101 moves transversely along the short part of the L slot 1102. Once twisted, the pin 1101 is trapped and cannot move upward, sealing the lid and bottom of the chamber together. The chamber can be opened again by a twisting action by a user in the direction opposite the twist used to lock the parts together.

As an exemplary use case, a stent retriever is placed in the bottom 101b of device 100 balanced on the support of hole 106 and support arm 105. The lid 101a is closed with sufficient force to engage the snap fit ring (again, see FIGS. 10-16 and accompanying description). The operator connects two syringes to the ports 102. At least one of the syringes containssaline or other suitable wash fluid. The syringes are actuated in turns to create turbulence in the chamber. The saline may be, for example, hospital grade saline, or heparinized saline. The turbulence physically debrides the stent retriever, removing most and typically all thrombus debris. Is it preferable that less liquid is used than the chamber can hold to ensure rapid movement of the fluid over the stent retriever. Next, a force is applied to the levers 107 to open the chamber 101. The now cleaned stent retriever is removed, ready for immediate reuse during the same procedure that soiled the stent retriever in the first place.

The device 100 reduces the time required to clean the stent retriever before re-insertion to under 15 seconds. In addition, the device may be used by a single operator without leaving the sterile operating field. With the possible exception of negligible leakage through hole 106/109, the device seals its contents during use such that neither the stent, wash fluid, or debris removed from the stent escape the chamber 101 while it remains closed. Once opened, the cleaned stent is ready for re-use, and any removed thrombus debris may be collected from the basin of bottom 101b.

The time required to open a sterile embodiment from its packaging, insert a stent, wash the stent, and remove the stent is generally less than or equal to ten seconds. Of course longer wash cycles may be performed, but exemplary embodiments require no more than 10 seconds of use to effectively clean a stent and have the stent ready for immediate reuse after the elapsed wash time.

A more specific exemplary sequence of steps of use is as follows. First, the packaging is opened and the device placed in the sterile field. Next, the chamber is opened using e.g. the thumb catches, unless the device is packaged in the open state, in which case no opening step is required. Next, the soiled stent retriever is placed in the main compartment (the chamber) by guiding the tail-wire across the notched post of the support arm and into the notch/hole in the lid. The stent retriever should be facing one or more of the luer connectors. Next the lid is closed, while ensuring that the tail-wire stays in the notch that permits it to extend out of the chamber. The snap fit ring is pressed closed until it snaps. At this point or before any step prior, two syringes are filled with e.g. 10 mL of saline each. Next, each syringe is attached to a luer connector port. Grasping one syringe in each hand, the plungers are alternatively depressed, similar to creating an agitated bubble chamber, for e.g. 5-15 seconds. The wash chamber may be angled with respect to gravity during use so that the saline in the chamber flows back into the syringes in order to create maximum turbulence. Next, the user may visually inspect the enclosed stent retriever through the clear lid of the chamber. If the blood clot or thrombus has not been removed from the stent retriever, further cycles of actuating the syringes may be performed. The user may gently shake the device if desired, knowing the support structure inside the chamber will generally keep hold of the stent retriever and prevent it from making contacts with the chamber walls. Once visual inspection through the wall of the chamber shows satisfactory cleanliness of the stent retriever, the thumb catches are used to open the chamber. The stent retriever is removed, and a final visual inspection of cleanliness may be conducted. The stent retriever is then ready for immediate reuse. If required or desired, the chamber with the dirty wash fluid may be tilted and the fluids extracted into one of the attached syringes to collect the thrombus and saline for composition analysis. Alternatively, the chamber can be attached to an external suction pump via one of the ports, and the saline or other liquid in the chamber may be aspirated out mechanically by the suction pump.

An exemplary wash device may be made in part or entirely from a plastic injection molded plastic, e.g. medical grade polypropylene. After manufacture, the device may be sealed in a sterile peel pouch (e.g., a Tyvek® peel pouch) until it is needed.

Generally, exemplary devices are well-suited for provision as sterile, single use devices. The most common methods for sterilizing medical devices are Ethylene Oxide (EtO), Gamma Irradiation, and wet or dry steam autoclaving. The materials may be polymers suitable for such sterilization procedures.

While not required of all embodiments, optically transparent materials are desirable for part of or else the entirety of the wash chamber. A window or else transparent walls allow the operator to visually inspect the results of the washing cycle without opening the device. Thermoplastics such as polycarbonate and polypropylene are suitable for this purpose. While polypropylene is not as optically transparent as polycarbonate, both would still allow visual monitoring of the cleaning.

While an exemplary device need not necessarily satisfy a specific Ingress Protection (IP) rating, some embodiment may be configured to satisfy such a rating, e.g. IP 65, 66, 67, or 68. An IP65 rated chamber, known as "dust tight" and protected against moderate jets of water, from any angle, may be used for example. In some embodiments, a deliberate opening such as the hole for the tail wire may be desirable to permit air to leave the chamber as its displaced by fluid being added to the chamber from the syringe or other fluid source.

Exemplary embodiments discussed above suggest the use of syringes as a fluid source. Syringes are advantageously an inexpensive and easily obtained medical supply. The wash device thus requires no power besides that of the human hand. However, exemplary wash devices may be connected (e.g., configured for connection with) fluid sources other than syringes. For example, a battery or wall powered device with motors may be connected. Pulsed lavage or other equipment for the creation of water jets or water propulsion may also be used. Though more expensive, such alternatives may be used when more forceful waterjets are desired in the wash chamber than may be possible with syringes. Such alternatives also may reduce the need for human actuation, which may be desirable by some users.

Figures 24A, 24B:
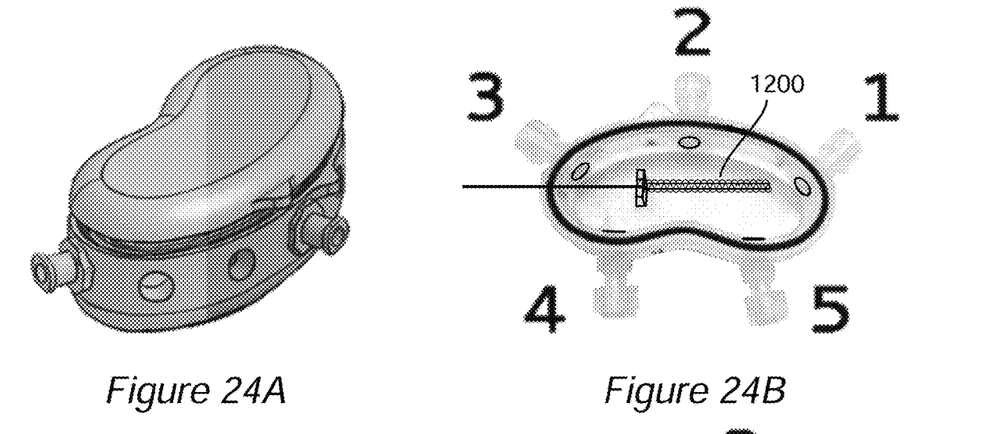
FIGS. 24A and 24B are views of a bean-shaped device with a plurality of different port positions.
Figure 25A:
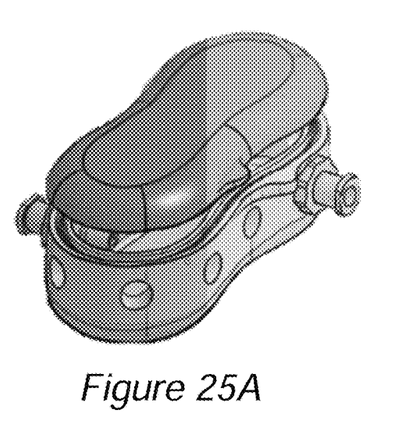
FIGS. 25A and 25B are views of a peanut-shaped device with a plurality of different port positions.
Figure 25B:
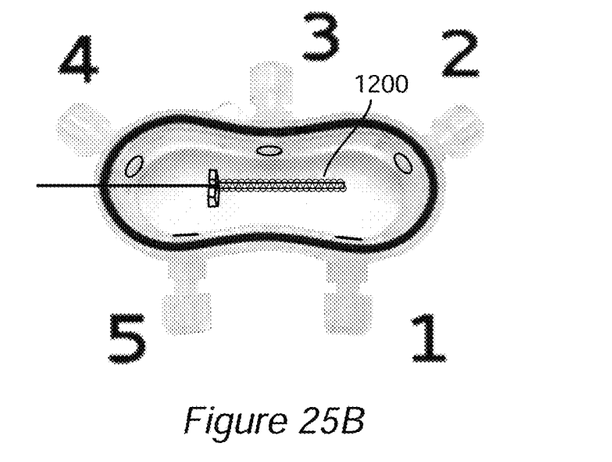
Figure 26A:
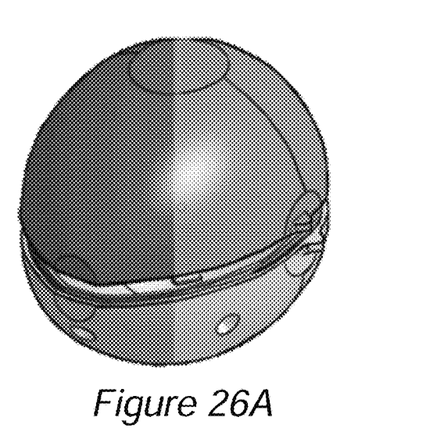
FIGS. 26A and 26B are views of an egg-shaped device with a plurality of different port positions.
Figure 26B:
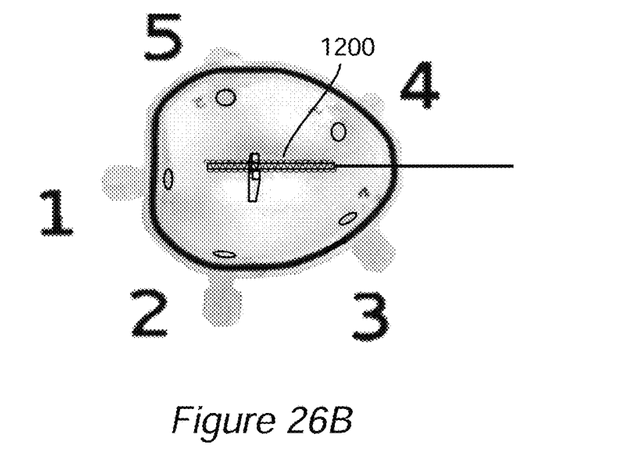

FIGS. 24A, 24B, 25A, 25B, 26A, and 26B are non-limiting illustrative examples of different chamber shapes and different port positions. In each of FIGS. 24B, 25B, and 26B a stent retriever 1200 is depicted seated in the respective cleaning device's support structure. The kidney-bean shaped configuration depicted in e.g. FIGS. 1A and 1B is but one exemplary shape of the wash device. Other shapes which may be used in alternative embodiments include but are not limited to peanut shape (FIGS. 25A and 25B), and egg shape (FIGS. 26A and 26B). Generally, however, bean-shaped (FIGS. 24A and 24B) was found to be especially advantageous from wash performance, ergonomics, and manufacturability perspectives.

The position of the ports on the device may vary among embodiments. FIGS. 24B, 25B, and 26B each have five ports illustrates (labeled 1 to 5 in each figure) as nonlimiting example positions. As depicted in FIGS. 1A and 1B, two exemplary positions are on the half of the device opposite the hole for the tail wire. More specifically, the ports are positioned on substantially the same plane as where the support structures causes a stent retriever to rest inside the chamber when the stent retriever is fully seated in the cradle of the support structure. The ports are on opposite sides of the long axis of the chamber and therefore on opposite sides of the stent retriever. In addition, the ports are angled e.g. 30-45 degrees off the longitudinal axis. Other port locations may be used for additional ports or instead of the exemplary port locations depicted in the figures. One alternative, illustrated by port 1 of FIG. 26B, is a port situated substantially parallel to an inserted stent retriever such that water admitted through the port may jettison directly down the center axis of the stent retriever. Another alternative—illustrated by e.g. ports 2, 4, and 5 of FIG. 24B as well as ports 1, 3, and 5 of FIG. 25B—is a port substantially transverse to the long axis of the stent retriever when the stent retriever is seated in the support structure.

Various attachments or nozzles may be made part of or attachable to the ports where fluid is admitted to the chamber, or else nozzles may be attached to syringes or other fluid sources prior to their attachment to the ports. Nozzles may be used to provide specific fluid stream characteristics, e.g., a nozzle with a smaller diameter hole than the port of the chamber may be used to increase pressure and flow rate of fluid being admitted to the device's chamber. Another example nozzle may be a spray head with micromachined holes, or holes produced by other means, to create a multiple streams at a single port, much like a shower head, turning one stream into multiple smaller streams with a higher pressure.

While exemplary embodiments of the present invention have been disclosed herein, one skilled in the art will recognize that various changes and modifications may be made without departing from the scope of the invention as defined by the following claims.

What is claimed is:

1. A device for cleaning a stent retriever within a sterile surgical field, comprising a chamber configured to receive and enclose the stent retriever to be cleaned, the chamber comprising a lid and a bottom, wherein the bottom is shaped as a cup or basin capable of retaining liquid and debris washed from the stent retriever, and wherein the bottom and the lid are attachable with one another to enclose the stent retriever inside the chamber and detachable from one another to insert or remove the stent retriever from the chamber;

at least one port configured for connection with a fluid source to enable inflow and/or outflow of a fluid to or from the chamber; and one or more support structures comprising a support arm projecting from a wall of the chamber, the support arm comprising a top end positioned entirely inside the chamber and configured to keep hold of the stent retriever in a fixed position inside the chamber and prevent the stent retriever from making contact with walls of the chamber, wherein the top end of the support arm comprises a cut-out configured to receive and keep hold of a tail wire of the stent retriever, wherein the cut-out is slightly smaller than a size of the tail wire and configured to clip in the tail wire.

2. The device of claim 1, wherein the chamber is configured to permit the tail wire of the stent retriever to extend out of the chamber while enclosing a remainder of the stent retriever.

3. The device of claim 2, wherein the one or more support structures comprises a hole or deformable seal at an edge of the chamber through which the tail wire extends.

4. The device of claim 1, further comprising a fastener configured to create a positive holding force which holds the bottom and the lid together.

5. The device of claim 4, further comprising one or more levers configured to reduce a user applied force required to overcome the holding force.

6. The device of claim 1, further comprising a snap fit ring configured to seal an interface between the bottom and the lid of the chamber for at least 95% of the interface.

7. The device of claim 1, wherein the chamber is sized to accommodate no more than one stent retriever at a time.

8. The device of claim 1, wherein the chamber has an internal volume of 30 ml or less.

9. The device of claim 1, wherein the device is handheld.

10. The device of claim 1, wherein the at least one port comprises a first port and a second port which permit simultaneous inflow of fluid to the chamber and outflow of fluid from the chamber.

11. The device of claim 1, wherein in a closed state, the device has a length of 3 to 5 inches, a maximum width of 1.5 inches, and a height of 1 to 2 inches.

12. The device of claim 1, wherein a part or an entirety of the chamber comprises optically transparent material allowing visual inspection into the chamber without opening the chamber.

13. The device of claim 1, wherein the lid and the bottom are permanently connected to one another by a hinge.

14. The device of claim 1, wherein the support arm is a post.

15. The device of claim 1, wherein the bottom comprises an exterior face that prevents rolling when the bottom is set on a table or medical tray.

16. A kit for a mechanical thrombectomy procedure, comprising a stent retriever comprising a stent attached to a tail wire; and a cleaning device for cleaning the stent retriever within a sterile surgical field, the cleaning device comprising a chamber configured to receive and enclose the stent retriever to be cleaned, the chamber comprising a lid and a bottom, wherein the bottom is shaped as a cup or basin capable of retaining liquid and debris washed from the stent retriever, and wherein the bottom and the lid are attachable with one another to enclose the stent retriever inside the chamber and detachable from one another to insert or remove the stent retriever from the chamber, at least one port configured for connection with a fluid source to enable inflow and/or outflow of a fluid to or from the chamber, and one or more support structures comprising a support arm projecting from a wall of the chamber, the support arm comprising a top end positioned entirely inside the chamber and configured to keep hold of the stent retriever in a fixed position inside the chamber and prevent the stent retriever from making contact with walls of the chamber, wherein the chamber is configured to be used to sufficiently remove the debris from the stent retriever to permit reuse of the stent retriever during a single thrombectomy procedure and to allow collection of the debris retained by the bottom of the chamber for pathological analysis, wherein the top end of the support arm comprises a cut-out configured to receive and keep hold of the tail wire of the stent retriever, wherein the cut-out is slightly smaller than a size of the tail wire and configured to clip in the tail wire.

17. The kit of claim 16, wherein the chamber is configured to permit a-the tail wire of the stent retriever to extend out of the chamber while enclosing a remainder of the stent retriever.

18. The kit of claim 17, wherein the one or more support structures comprises a hole or deformable sealing surface at an edge of the chamber through which the tail wire extends.

19. The kit of claim 18, wherein the stent retriever is insertable into and retainable by the cleaning device with only two places of contact between the stent retriever and the cleaning device, wherein the two places are (i) the support arm and (ii) the hole or deformable sealing surface at the edge of the chamber through which the tail wire extends.

* * * * *